United States Patent [19]

Secker

[11] Patent Number: 5,188,108

[45] Date of Patent: Feb. 23, 1993

[54] SENSOR, APPARATUS AND METHOD FOR NON-INVASIVE MEASUREMENT OF OXYGEN SATURATION

[75] Inventor: Herbert Secker, Stuttgart, Fed. Rep. of Germany

[73] Assignee: Hewlett-Packard Company, Palo Alto, Calif.

[21] Appl. No.: 645,042

[22] Filed: Jan. 23, 1991

[30] Foreign Application Priority Data

Feb. 15, 1990 [EP] European Pat. Off. ........ 90102954.6

[51] Int. Cl.⁵ .............................................. A61B 5/00
[52] U.S. Cl. .................... 128/633; 128/666; 356/41
[58] Field of Search .................. 128/633, 664–666; 356/41; 250/341, 345

[56] References Cited

U.S. PATENT DOCUMENTS

| | | | |
|---|---|---|---|
| 4,714,341 | 12/1987 | Hamaguri et al. | 356/41 |
| 4,942,877 | 7/1990 | Sakai et al. | 128/633 |
| 5,057,695 | 10/1991 | Hirao et al. | 128/633 |

FOREIGN PATENT DOCUMENTS

| | | |
|---|---|---|
| 0329196 | 8/1983 | European Pat. Off. . |
| 0135840 | 8/1984 | European Pat. Off. . |
| 0353619 | 7/1989 | European Pat. Off. . |
| 08901758 | 9/1989 | European Pat. Off. . |
| 3328862A1 | 3/1985 | Fed. Rep. of Germany . |

Primary Examiner—Kyle L. Howell
Assistant Examiner—Robert L. Nasser, Jr.
Attorney, Agent, or Firm—Perman & Green

[57] ABSTRACT

A sensor for non-invasive measurement of oxygen saturation using the reflection method comprises a red transmitter (55), an infrared transmitter (58) and a receiver (57). The distances between the transmitters and the receiver are selected such that the length of the light path (60, 61) between the red transmitter (55) and the receiver (57) is substantially equal to the length of the light path (62, 63) between the infrared transmitter (58) and the receiver (57). The sensor comprises a further red transmitter (56) which is used for another application at the human body or another tissue characteristics where the depth of penetration at the various wavelengths is different from the shown example. Together with an appropriate oximeter, manual or automatic adaptation is possible. Further signal improvement may be obtained by autocorrelating the received signal, detecting its frequency and cross-correlating it with a pattern function of the same frequency.

36 Claims, 11 Drawing Sheets

SENSOR, APPARATUS AND METHOD FOR NON-INVASIVE MEASUREMENT OF OXYGEN SATURATION

The present invention relates to a sensor, an apparatus and a method for performing non-invasive measurements of oxygen saturation based on the reflection technique.

Oxygen saturation is a clinically very relevant parameter to assess the condition of a patient. Particularly in the operating room, the oxygen saturation of the blood gives an indication of the patient's condition, its supply with oxygen and other physiological factors.

One possibility to obtain a very precise value of the patient's oxygen saturation is to take a blood sample and analyze it in a blood gas analyzer. Despite the high precision of this method, it is an invasive technique and this means that it cannot performed frequently, i.e. does not allow continuous monitoring. Therefore, significant changes in the oxygen saturation value may be missed. Last not least, it is understood that an invasive technique is not the preferred way to monitor a patient.

It is therefore highly desirable to measure oxygen saturation non-invasively. This can be achieved by a technique called oximetry.

An oximeter usually comprises two or more light sources of different wave length. The light is irradiated on human flesh, and either the intensity of the light transmitted through the flesh, or the intensity of the reflected light is measured. In more general terms, "light" does not only mean electromagnetic waves in the visible spectrum. For example, the most common oximeters use one wavelength in the visible spectrum and another wavelength in the infrared spectrum.

The light transmitted or reflected by human flesh is attenuated according to Lambert-Beer's law, i.e.

$$I = I_0 e^{-Ecl} \quad (1)$$

wherein I represents the intensity of the received light, $I_0$ the intensity of the incident light, E the molecular extinction coefficient, c the concentration of the absorbing species and l the thickness of the absorbing layer, i.e. the length of the light path through tissue.

If we assume that human tissue contains components with constant characteristics over time—such as bones, muscles etc.—, and components with time-varying characteristics—i.e. blood—, equation (1) yields $$\ln\left(1 \frac{I_{AC}}{I_{DC}}\right) = -Ec\, l(t) \quad (2)$$

wherein $I_{DC}$ represents a component constant over time (caused by absorbers of constant absorbance), $I_{AC}$ represents the time-varying component (caused by blood) and l(t) represents the variation in thickness caused by arterial pulsations. This equation contains two unknown values, c and l(t).

As oxygen saturation is defined as the quotient of the concentration of oxyhemoglobin in relation to the concentration of total hemoglobin, i.e.

$$SaO_2 = \frac{c_{HbO2}}{c_{Hb} + c_{HbO2}} \quad (3)$$

(wherein $c_{HbO2}$ is the concentration of oxyhemoglobin and $c_{Hb}$ is the concentration of reduced hemoglobin), two absorbing species have to be taken into consideration. In this case, equation (2) becomes $$\ln\left(1 - \frac{I_{AC}}{I_{DC}}\right) = -(E_{Hb}c_{Hb} + E_{HbO2}c_{HbO2})\, l(t) \quad (4)$$

with $E_{Hb}$=the molecular extinction coefficient of reduced hemoglobin and $E_{HbO2}$=the molecular extinction coefficient of oxyhemoglobin. It can be easily seen that, in this case, we have three unknown values, $c_{Hb}$, $c_{HbO2}$ and l(t).

A measurement at two different wavelengths allows to determine oxygen saturation. In fact, measurement at two wavelengths results in two equations for three unknown values, but due to the definition of oxygen saturation one of these values cancels out.

As the oxygen saturation value depends also on empirical constants, the two equations obtained from equation (4) (for both wavelengths) are used to calculate a ratio R which, in turn, is used to calculate $SaO_2$.

For more details on the theory of oxygen saturation measurement, reference is made to former publications on this subject, e.g. U.S. Pat. No. 4,167,331 or EP-A-262 778 (the latter patent application contains a quite complete breakdown of the theory).

Up to now, most oximeters on the market use the transmission technique, i.e. measure the intensity of the light transmitted through a human organ like the earlobe or the finger. Although the obtained measurement results still are not comparable with the precision of blood sample analysis, this technique even yields better results than the reflection technique. Regarding reflection oximeters, reference is made to EP-A-135 840 which depicts a reflection sensor for the fetus. The reflection technique has also been used to measure other physical quantities such as metabolism, see e.g. U.S. Pat. No. 4,223,680.

In fact, monitoring a fetus prior to and under birth is an application requiring the reflection technique because it is not possible to place a transmitter on one side of the fetal scalp and a receiver on the other side (besides that, the results would be unusable as the tissue absorbs most of the incident light on a length of approximately 10 cm). The same is true for an adult patient in shock; due to the effect of centralization of the blood, meaningful results can in this case only be obtained from a transducer applied to the trunk (i.e. a reflection transducer), and not from a transducer applied to a limb. Still the results of the reflection technique are more than modest, and no clinically usable reflection sensor has been developed up to now.

It is therefore a major objective of the present invention to provide a sensor and an apparatus for measuring the oxygen saturation based on the reflection technique with a precision sufficient for clinical application. It is also an objective of this invention to provide a method therefore.

According to the present invention, the inventor has recognized that the depth of penetration of human tissue is not identical for all wavelengths, i.e. the length of the light paths at various wavelengths is *different* even if we assume that the transmitters and/or the receivers could be placed at exactly the same point. Therefore, prior art oximeters which used two transmitters in the same distance to a receiver made a systematic error due to the different lengths of the light waves in the tissue as variables were treated identical (according to theory) although they were actually not. This may be an explanation for the unsatisfying performance of prior art oximeters.

The present invention proposes to use a sensor for non-invasive measurement of oxygen saturation by irradiating human tissue with electromagnetic waves and measuring the intensity of the reflected waves comprising carrier means, at least two transmitters emitting electromagnetic waves of different wavelengths into the human tissue and mounted on said carrier means, and at least one receiver set up to receive electromagnetic waves of said different wavelengths reflected from the human tissue and mounted on said carrier means, wherein said at least two transmitters are mounted on said carrier means in distances selected such that the lengths of the light paths through the human tissue at both different wavelengths are substantially equal. The length of a light path through tissue at a certain wavelength may be determined empirically, or by calculation if the angle of irradiation and the extinction coefficient at a certain wavelength is known, and the basic idea of the invention is to do this for at least two wavelengths and to mount the transmitters such on the carrier means that the lengths of the light paths are substantially equal.

By such construction, the assumptions of the theory are perfectly met. Particularly, the assumption that the length of a light path through tissue cancels out because the lengths of the light paths at both (or more) wavelengths are equal, is fulfilled. Therefore, the invention allows a considerably more precise measurement of oxygen saturation with a reflection sensor. It has to be particularly emphasized that, in transmission oximetry, the systematic error encountered by different light paths is limited as there are usually two transmitters located very close to each other and a receiver located on the opposite side of the human limb so that the light paths, although not identical, are very close to each other. This does *not* apply in case of reflection oximetry due to the differing depth of penetration at various wavelengths. Therefore, the basic idea of the present invention is more important for application in reflection oximetry, than it is for transmission oximetry.

It has already been mentioned that the length of the light path through human tissue at a certain wavelength—or the depth of penetration instead—may be determined empirically. It is also possible to calculate the depth of penetration or the length of the light path mathematically on the basis of known extinction coefficients at various wavelengths and for certain tissue. The transmitter with the smaller extinction coefficient, i.e. smaller absorbance and therefore larger depth of penetration is placed closer to the receiver than the transmitter emitting light incorporating a larger extinction coefficient. If electromagnetic waves in the range of 650 nanometers (nm) and 940 nm are used (red and infrared light), the transmitter emitting infrared light is usually placed closer to the receiver than the transmitter emitting red light, as infrared light penetrates human tissue deeper than red light. However, there may also be cases where the actual distance—measured on the surface of the sensor—between the infrared transmitter and the receiver is not smaller than the distance between the red transmitter and the receiver. This may e.g. be caused by a certain geometry of the sensor or the angle of inclination of a transmitter and/or receiver.

It is understood that the invention as described above requires that the transmitters are operated in pulsed mode if only one receiver, sensitive to all used wavelengths, is used. Instead, it is also possible to use a selective receiver or more than one receiver.

The basic idea of the present invention may also be "reversed". In this case, we have a sensor for non-invasive measurement of oxygen saturation by irradiating human tissue with electromagnetic waves and measuring the intensity of the reflected waves comprising carrier means, at least one transmitter emitting electromagnetic waves of different wavelengths into the human tissue and mounted on said carrier means, and at least two receivers set up to receive electromagnetic waves, each of these receivers being sensitive to at least one of said different wavelengths reflected from the human tissue and mounted on said carrier means, wherein said at least two receivers are mounted on said carrier means in distances selected such that the lengths of the light paths through the human tissue at both different wavelengths are substantially equal. If only one transmitter is used, this must be a transmitter able to emit light of at least two different wavelengths, e.g. a red/infrared light-emitting diode (LED), or it must be a broadband transmitter.

In both of the above cases, it is particularly advantageous to use sensors with carrier means adapted for application to a specific part of the human body (e.g. a limb). In such case, the transmitters and/or receivers can be placed in distances specifically adapted to average values of tissue characteristics of said specific human limb. This yields better measurement results than a general-purpose sensor as the structure of the tissue (skin, fat, muscles, bones) may be different depending on the place of application. An even more feasible solution is to adapt the carrier means to a specific human limb by a certain geometry, such as a finger sensor with the carrier means substantially closed in itself in cross-section for application to a finger. Such sensor can necessarily only be applied to the human limb for which it is designed (a finger sensor can e.g. not be applied to a nose of a patient), so that erroneous readings due to faulty application by medical personnel can be avoided.

Another example of a sensor adapted for a specific application is a fetal sensor, i.e. a sensor adapted specifically for monitoring of a fetus prior to and under birth. Such a sensor comprises a cap with integrated transmitter(s) and receiver(s) wherein the lengths of the light paths at the various wavelengths are substantially equal. The cap is fixed at the fetal scalp either by a medical (surgical) glue or—in a preferred embodiment—by means of underpressure, i.e. a suction tube connected with a suction source. It goes without saying that the present invention is of particular importance for fetal oxygen saturation measurement which requires a reflection sensor. The invention makes it therefore possible to obtain reliable oxygen saturation readings also when monitoring a fetus, particularly in critical phases of labour.

In case the sensor is adapted for application to a certain part of the human body, such feature can be used to control correct application of the sensor. The received values can be compared with empirical data typical for the place of application (and/or the age of the patient, its sex, etc.), and if there is a significant deviation either indicating the wrong place of application or a not tightly attached transducer, generate a warning message to the user. The invention therefore also relates to an apparatus for non-invasive measurement of oxygen saturation comprising conversion means converting the intensity of the received electromagnetic waves into electrical signals, processing means for the calculation of oxygen saturation from said electrical signals, and plausibility checking means comparing the received signals with predefined limits or predefined signals and generating an alarm or a warning message upon a significant deviation. The comparison between the actual and the sample data may be performed using any convenient technique, e.g. comparison of amplitudes, frequency components, of the shape of the signals using correlation techniques etc.

This leads to another important aspect of the present invention. A significant improvement in signal quality may be attained in that the place of application of the sensor is detected and in that the measured values are appropriately corrected. The invention proposes to use sets of predefined signals representative of certain places of application at the human body or representative of certain tissue characteristics and selecting—based on the above mentioned criteria such as amplitude or shape—the set incorporating the most common characteristics with the received signals, and then to correct these signals in dependency of the selected set. The sets of predefined signals may either represent attenuation values of one or more wavelengths, amplitudes of the alternating components or signal shapes. Such detection of the place of application or of a certain tissue characteristic, and appropriate correction, yields considerably better oximeter readings. It has to be pointed out that detection of tissue characteristics and appropriate correction is even useful for a sensor which is—by means of its geometry—adapted for use at a specific human limb; the reason is that there may be differences in tissue characteristics from patient to patient, even if the selected place of application is the same, e.g. caused by the age of the patient or its condition (patients in shock show significant differences, compared to other patients; furthermore, only reflection oximetry is possible in such case as a sensor applied to an arm, a finger or a leg would—due to lack of pulsating blood—not yield meaningful readings).

The above idea to take the differing lengths of the light paths at various wavelengths into account can be broadened to a sensor comprising at least one first transmitter emitting electromagnetic waves of a first wavelength and at least two second transmitters emitting electromagnetic waves of a second wavelength, wherein said first and second transmitters are mounted on carrier means in different distances to said at least one receiver such that the length of the light path through the human tissue between said first transmitter and said receiver is for tissue with a certain predefined characteristics substantially equal to the length of the light path through the human tissue between the first of said second transmitters and said receiver, whereas the length of the light path through the human tissue between said first transmitter and said receiver is for tissue with another certain predefined characteristics substantially equal to the length of the light path through the human tissue between the second of said second transmitters and said receiver. Such a sensor may be useful as a multi-purpose sensor (multi-application sensor), in which case the first of said second transmitters is operated in one application and the second of said second transmitters in another application. The correct place of application—and, therefore, the one of said second transmitters to be operated—may either be predefined by manual entry, or may be selected by automatic operation of the associated oximeter, as will be described below.

Even if adapted for a specific application (where the selected place of application (e.g. the chest) is the same for all patients), the above sensor may be used to operate precisely with patients of different tissue characteristics. Further, it is understood that the above idea may also be expanded to a sensor with three, four, five etc. second transmitters in order to provide a greater variety of sensor application/tissue characteristics. It is also understood that there must be not necessarily only one first transmitter; instead, also a multiplicity of first transmitters may be used. In a preferred embodiment, a sensor of this type comprises two first and two second transmitters arranged symmetrically with respect to the receiver, e.g. an unsymmetrical square or rectangle, or 2n first transmitters and 2n second transmitters.

It is understood that the idea of a sensor with light paths adapted—in terms of their length—may also be reversed, i.e. relate to a sensor comprising at least one first and at least two second receivers and (at least) one transmitter. The various receivers in this case are placed such that the length of the light path through the human tissue between the transmitter and the first receiver is for tissue with a certain predefined characteristics substantially equal to the length of the light path through the human tissue between the transmitter and the first of the second receivers, whereas the length of the light path through the human tissue between the transmitter and the first receiver is for tissue with another certain predefined characteristics substantially equal to the length of the light path through the human tissue between the transmitter and the second of the second receivers.

The type of sensor described above with at least more than one light path of a certain wavelength through human tissue, where one of these light paths can be selected dependent on the application or the structure of the tissue, may also be adapted for application to a specific part of the human body (e.g. a limb), particularly by means of a certain geometry. For fetal application, such a sensor preferably comprises carrier means in form of a cap comprising at least two first transmitters, preferably light emitting diodes, emitting electromagnetic waves of a certain first wavelength, as well as at least two second transmitters, preferably light emitting diodes, emitting electromagnetic waves of a certain second wavelength, and at least one receiver responsive to said different wavelengths. The cap may be fixed on the fetal scalp by a surgical glue or by underpressure.

The invention also relates to an apparatus for operating a sensor with more than one light path of a certain wavelength. Such apparatus may comprise conversion means converting the intensity of the received electromagnetic waves into electrical signals, processing means for the calculation of oxygen saturation from said electrical signals, selection input means for selecting the place of application at the human body, and transmitter/receiver selection means responsive to said selection input means and set up to select certain transmitter(s) and/or certain receiver(s) depending on the place of application. When such an apparatus is used in conjunction with one of the aforementioned sensors, the operator may enter the actual place of application, e.g. the chest, the fetal scalp and so on, using the selection input means, and said transmitter/receiver selection means select then the appropriate transmitters for this application. Furthermore, other physiological parameters may be entered such as sex, patient's age or its condition. This allows very precise adaptation to the conditions of measurement by selecting the appropriate transmitters/receivers and therefore of the light paths. To ensure the high precision of such oximeter readings, plausibility checking means may be further provided which compare the received signals with predefined limits or predefined signals representative of the selected place of application and generating an alarm or warning message upon a significant deviation. It can thereby be avoided that errors caused by the medical personnel have any negative impact on oximeter readings.

Instead of manual entry of the place of application or other physiologically important values, an advantageous solution proposes to use an apparatus comprising conversion means converting the intensity of the received electromagnetic waves into electrical signals, processing means for the calculation of oxygen saturation from said electrical signals, and application detection means set up to select sequentially certain transmitter(s) and/or certain receiver(s). For each selection of a certain transmitter and a certain receiver, the obtained electrical signals specific to this selection are compared with sets of predefined signals representative of certain places of application at the human body or representative of certain tissue characteristics. The specific electrical signal comprising most common characteristics (amplitude, shape, ...) with a certain of these sets is then selected, and as this specific electrical signal is associated with a certain transmitter and/or receiver, these are selected by selection means for further measurement. Such an automatic adaptation system may be used for all kinds of applications, patients and tissue characteristics; it always selects the best possible transmitter/receiver combination for a particular kind of measurement. The only limitation is the number of stored sets of predefined signals.

Advantageously, the reflection sensors described up to now are also prepared to measure other physiological parameters. This is of particular importance if a sensor is specifically suited for a certain kind of measurement where the physiological conditions are known. This applies e.g. to a fetal sensor in the form of a cap; as another parameter of high interest for the evaluation of the fetal condition is the electrocardiogram (ECG), such a cap advantageously also provides electrocardiogram contacts.

The present invention also relates to a method for improving the signal quality of a noisy oximeter signal. Despite the considerable improvements achieved by a sensor and an apparatus described so far, it may happen that the received signal contains spectral noise components—e.g. caused by bad electrode contact or interference from power lines—or artefacts (e.g. caused by patient movement). Further, it may happen that the alternating component of the received signal is extremely small compared to the direct component so that it is difficult to detect the amplitude of the alternating component for the purpose of oxygen saturation calculation.

An advantageous solution proposed here for reliable detection of oxygen saturation even in noisy or disturbed signals relates to a method of calculating oxygen saturation from the intensity of electromagnetic waves of at least two different wavelengths reflected by or propagated through human tissue, wherein the intensities of the received electromagnetic waves are converted into electrical signals, and then an autocorrelation is performed on at least one (hereinafter called "one specific") of said electrical signals.

As known per se, autocorrelation is a mathematical operation stressing or amplifying periodic components, i.e. the *effective* components in a signal. In the present invention, autocorrelation is used to amplify the peaks caused by the arterial pulse which was formerly hidden in a noisy background.

Thus, it is possible to trigger on the peaks of the autocorrelated signal, i.e. to detect the frequency of the specific electrical signal from the autocorrelation function. This is a useful parameter per se because this frequency represents the heart rate. It is thus possible to detect the heart rate without ECG electrodes and/or as a by-product of oxygen saturation measurement.

The inventive method further provides a predefined signal, i.e. a standard function which is selected to be typical for an electrical signal received during oxygen saturation measurement. According to the inventive method, a predefined signal of substantially the same frequency as detected during the analysis of the autocorrelation function has to be used. This may be achieved in several ways; for example, a multiplicity of predefined signals, all equivalent in shape, but compressed/expanded in time with respect to each other, may be used. In this case, those of the predefined signals with a frequency substantially equal to that detected from the autocorrelation function is selected. Another, preferred solution provides only one predefined signal, and this signal is either compressed or expanded such that it incorporates substantially the same frequency as the autocorrelation function (which is the frequency of the previously mentioned specific electrical signal).

The specific electrical signal and the selected or generated predefined signal are now cross-correlated with respect to each other. The mathematical operation of a cross-correlation provides amplification of the useful, i.e. expected components in the signal and suppression of artefacts and noise provided the functions cross-correlated with each other have substantially the same frequency. Thus, if the frequency of the specific electrical signal can be reliably detected, cross-correlation with said predefined signal of substantially the same frequency removes the unwanted components from the signal. It is now easier to detect the maximum amplitude of the cross-correlation function and to use said maximum amplitude to calculate oxygen saturation. Due to the clear and undisturbed maximum amplitudes of the cross-correlation function, it is possible to indicate a reliably reading of oxygen saturation even from a noisy signal or a signal containing artefacts.

It is understood that this method is particularly useful for reflection oximetry where the signal quality is worse than in transmission oximetry. Particularly, a combination with the above described sensors and methods yields excellent results. However, it has to be emphasized that the method of performing an autocorrelation on the received signal, extracting the frequency thereof, selecting a standard function with the same frequency and cross-correlating this standard function with the received signal also yields considerable signal improvement even if not combined with one of the aforementioned sensors and methods. The technique described here is even very useful for transmission oximetry, particularly for signals hidden in a noisy background or disturbed by artefacts.

According to an advantageous embodiment, further signal improvement may be obtained if a set of predefined signals is provided, each predefined signal serving as a standard function (i.e. an ideal signal) for a certain place of application of the sensor. According to an improvement of the inventive method, the place of application of the sensor is entered by the user, and a predefined signal is selected from said set of predefined signals in dependency of the place of application of the sensor. Said selected predefined signal is then used for cross-correlation with the received signal. As in this case the standard function is specifically adapted to the place of application, it can be optimized for this specific application and therefore yields even better results.

In another preferred embodiment, a set of pattern signals representative of certain places of application at the human body or representative of certain tissue characteristics is provided. The specific received electrical signal is compared with said pattern signals, and the pattern signal comprising most common characteristics with said specific electrical signal is selected as predefined signal. This method therefore provides an automatic selection of the standard function in dependency of the incoming signal. This automatic adaptation may e.g. be used to detect the place of application or the tissue characteristics in a multi-purpose sensor; even in case of a sensor adapted for a specific application to the human body, it may be used either to check the correct application and/or to distinguish between different tissues depending on age, sex etc. of the patient. For example, a finger sensor for an adult person could also be applied to the arm of a neonate, and according to the described method, the oximeter is able to distinguish between these different applications and take appropriate corrective action.

The selection of a certain pattern signal from said sets of pattern signals may be performed in different ways, e.g. by comparing their amplitudes with the incoming signal. However, a preferred solution is to perform sequential cross-correlations between the received electrical signal and each pattern signal in said set of pattern signals. This provides a comparison of the *shape* between the actual and the standard functions which is a very powerful parameter.

It is understood that the above methods of performing cross-correlations may either be performed on the signal representing one specific wavelength only, or—preferably—on all of the received signals. However, it may turn out that the signal quality at a specific wavelength is satisfying and needs no further signal improvement; in such case, the above described method need only be performed on the signal corresponding to the other wavelength. Further, it may turn out that, although a cross-correlation between the received signal and a predefined or pattern signal results in significant improvement of the oxygen saturation reading, an autocorrelation is not necessary to detect the frequency of the received signal (that is, the received signal is of sufficient quality to trigger on it (detect its frequency) directly). The present invention also relates to such embodiment.

The present invention also comprises an apparatus for noninvasive measurement of oxygen saturation from the intensity of electromagnetic waves of at least two different wavelengths reflected by or transmitted through human tissue and comprising conversion means (converting the intensity of the received electromagnetic waves into electrical signals), autocorrelation means (performing an autocorrelation on at least a specific one of said electrical signals), frequency detection means (detecting the frequency of the autocorrelation function), frequency adaptation means (adapting the frequency of a predefined signal to the frequency of the autocorrelation function), cross-correlation means (cross-correlating said specific electrical signal and said predefined signal), detection means (detecting the maximum amplitude of said cross-correlation function), and oxygen saturation calculation means (calculating oxygen saturation from said maximum amplitude). The frequency detection means may comprise a peak trigger with a constant or adaptive trigger level to detect the peaks of the autocorrelation function, calculate the time delay between such peaks and the pulse frequency as the inverse of such time delay. The frequency adaptation means stretch or compress the frequency of the predefined signal so that it incorporates the same frequency as the received signal. Such frequency adaptation may be performed either by removing certain samples in the digitally stored signal (e.g. removing every second sample doubles the frequency)—this results in a compressed signal, i.e. a signal of a higher frequency; or there may be performed an interpolation between certain samples thus expanding the signal which is the same as lowering the frequency. It is understood that the frequency adaptation means could instead also make a selection among certain predefined signals equivalent in shape but different in frequency.

The detection means may also comprise a peak trigger to detect the maximum amplitude of the cross-correlation function. Such maximum amplitude is then used to calculate oxygen saturation. It is understood that means may also be provided to detect the minimum amplitude of the cross-correlation function; this is particularly useful in pulse oximetry where the information of oxygen saturation is calculated using the direct and the alternating components of the signals at each wavelength. The difference between maximum and minimum amplitude gives an indication of the AC-component, and the minimum amplitude an indication of the DC-component.

In one preferred embodiment, such apparatus comprises also sensor application input means which allow the user to enter the place of application of the sensor at the human body. This information is used by predefined signal selection means which select a predefined signal from a set of predefined signals in dependency of the place of application. In this environment, the apparatus may select a predefined signal specifically representative of the certain place of application at the human body selected by the user.

Alternatively, the apparatus may comprise pattern signal comparison means which compare the specific electrical signal with sets of pattern signals representative of certain places of application at the human body or representative of certain tissue characteristics. If the primary criterion is the shape of the signal, such comparison may be performed by cross-correlation means. Predefined signal selection means then select the pattern signal comprising most common characteristics—e.g. the highest amplitude in the cross-correlation function—with said electrical signal as predefined signal. This is again an "adaptive" apparatus able to select an "optimum function" as reference in dependency of the specific application or tissue characteristics.

The autocorrelation of the received electrical signal may also be omitted in this case if the received signal has sufficient quality to trigger directly on it, i.e. calculate its frequency without further signal processing.

Preferred embodiments of the invention will now be described—by way of a non-limiting example—with reference to the accompanying drawings in which.

Figure 5:
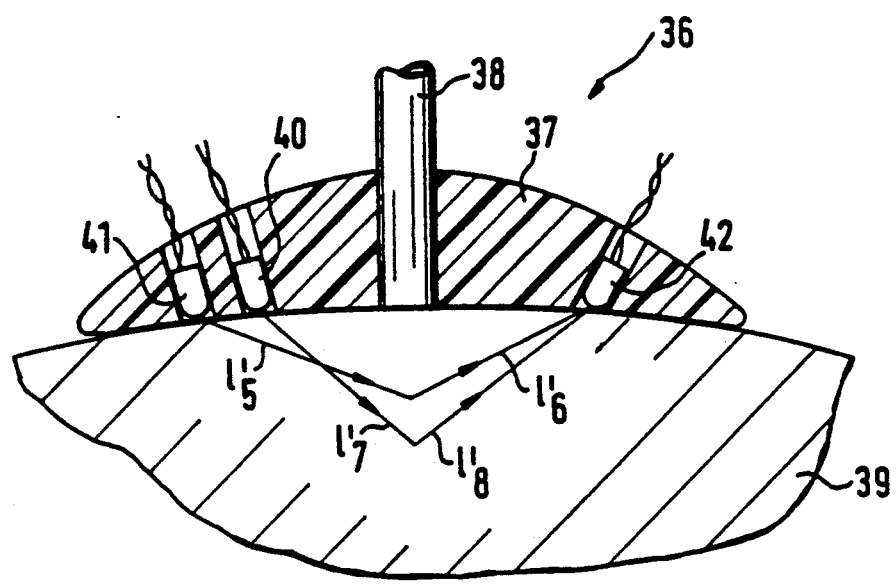
Figure 6:
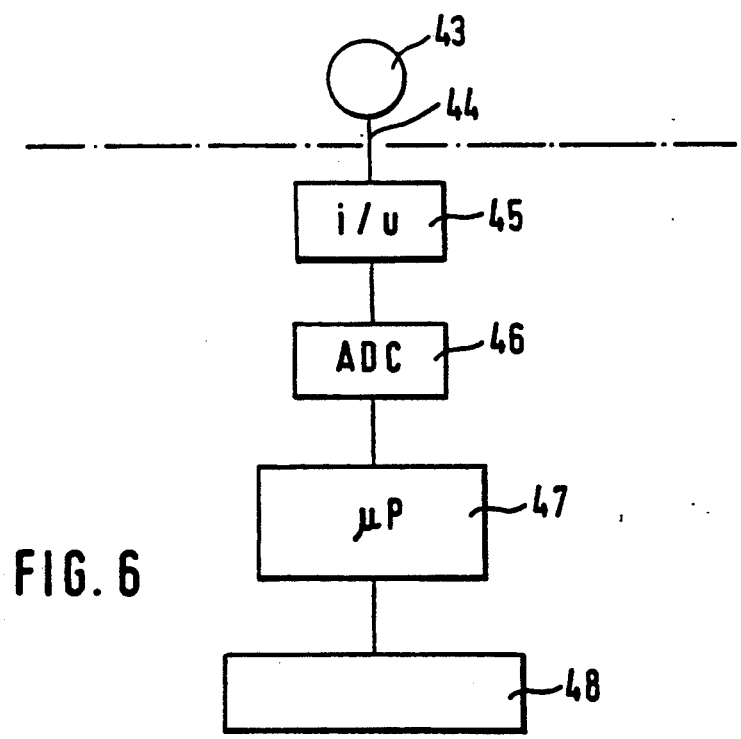
Figure 7A:
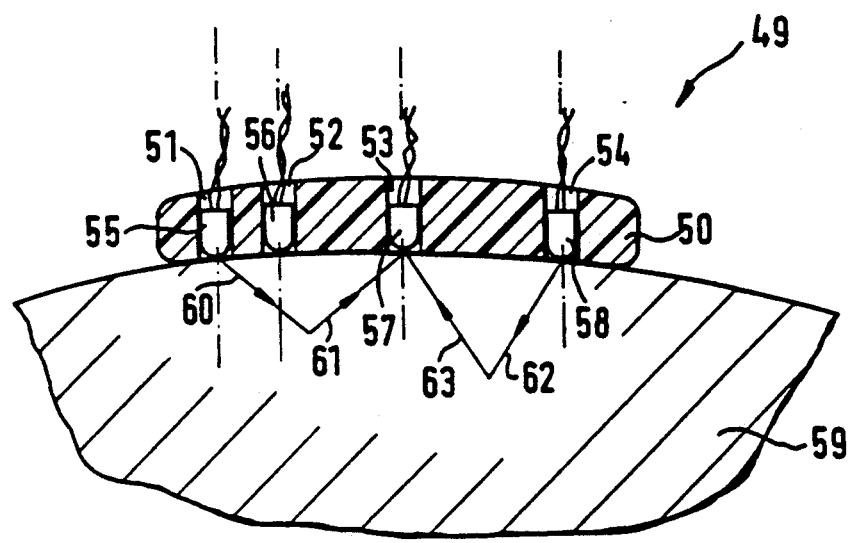
Figure 7B:
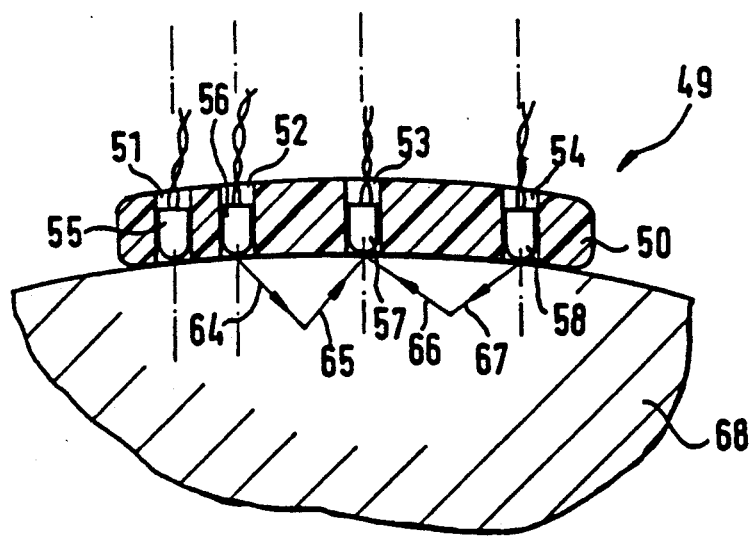
Figure 9:
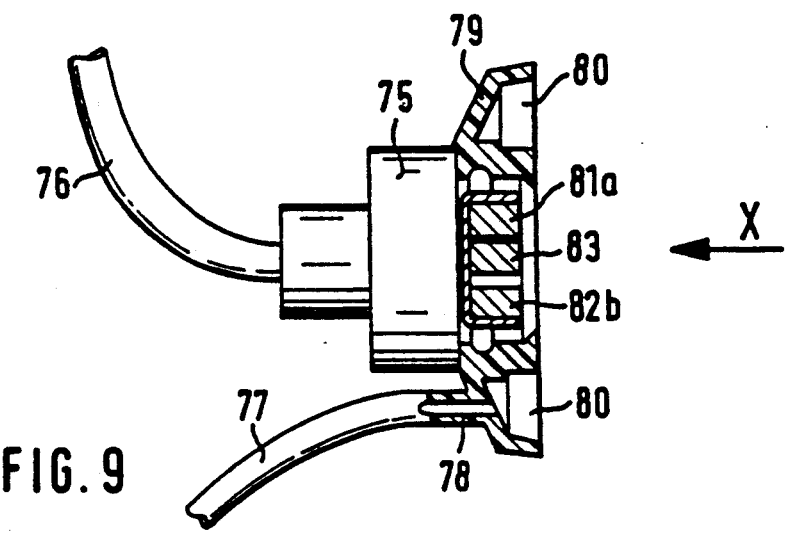
Figure 10:
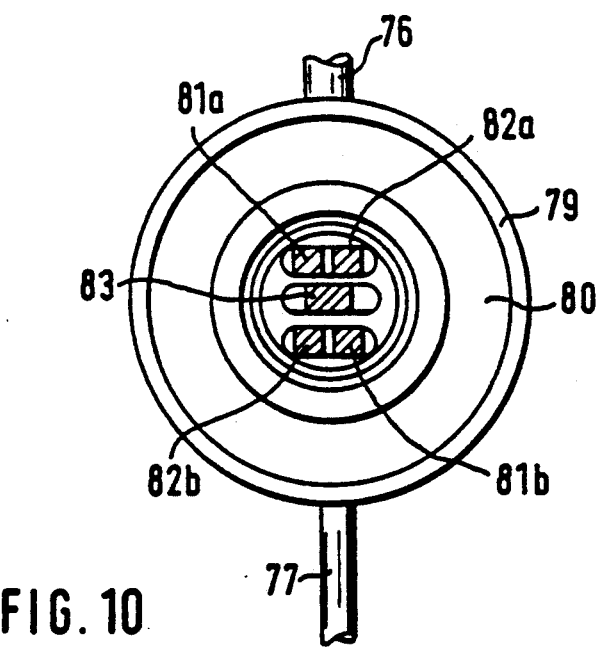
Figure 11:
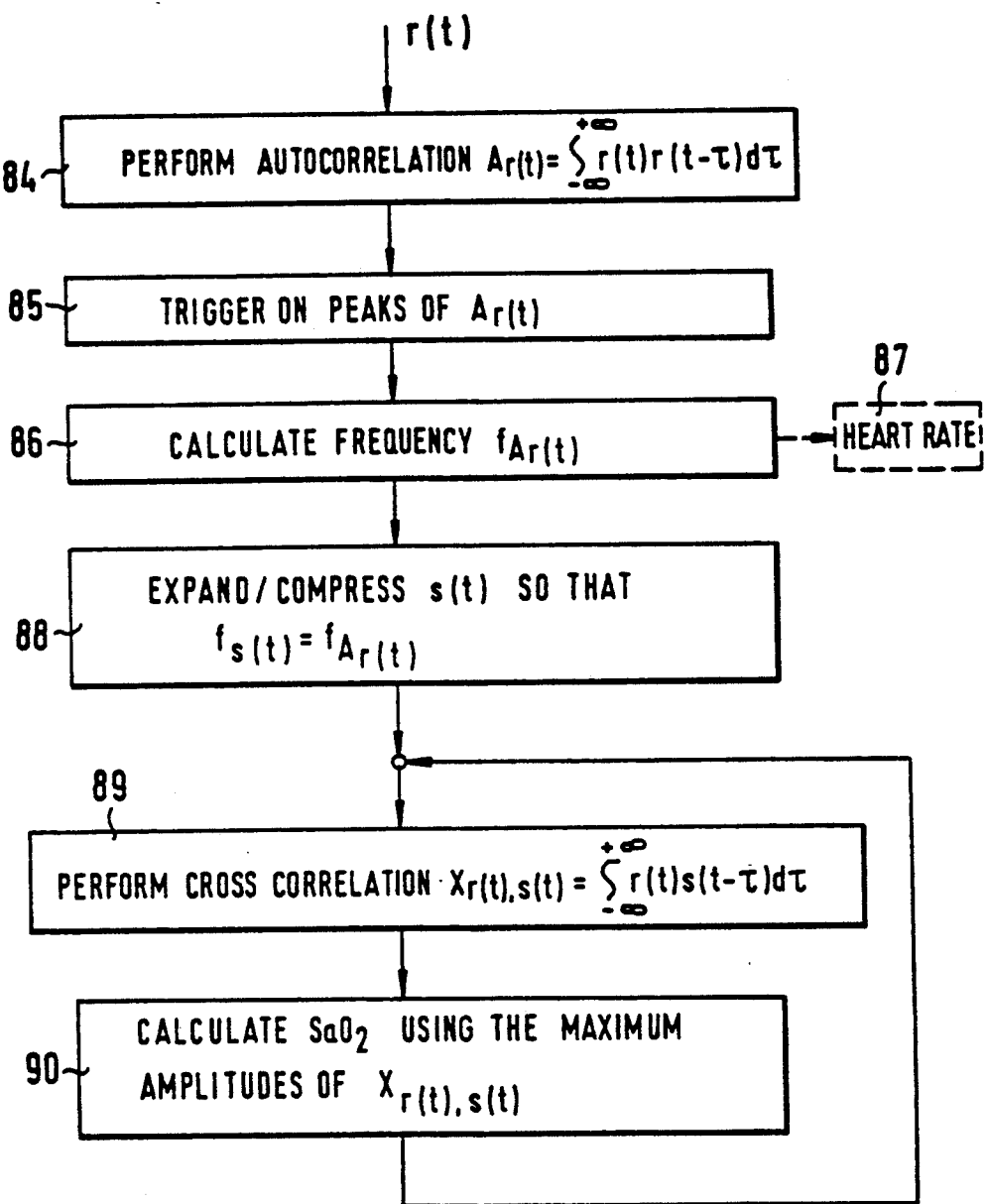
Figure 12A:
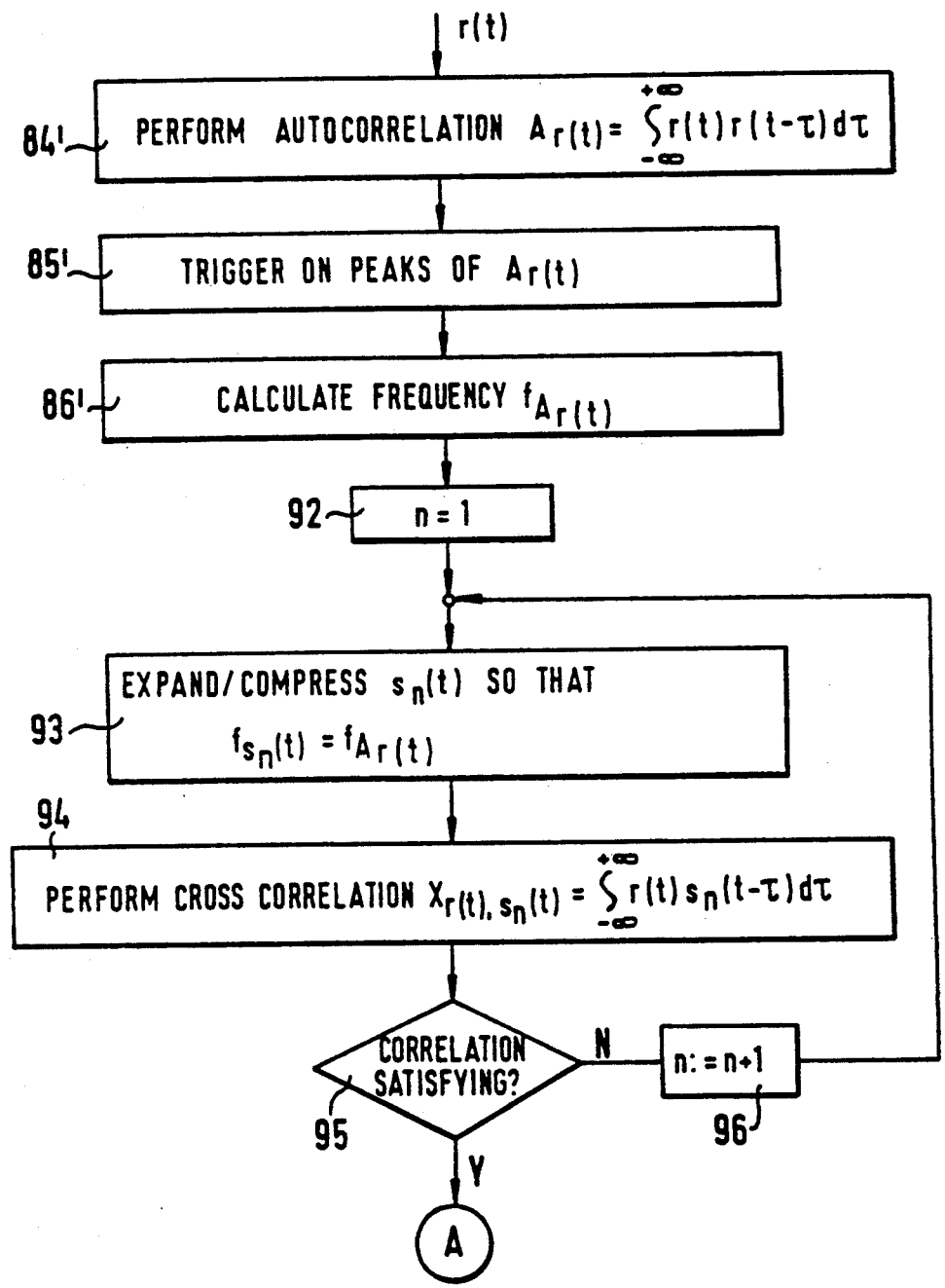
Figure 12B:
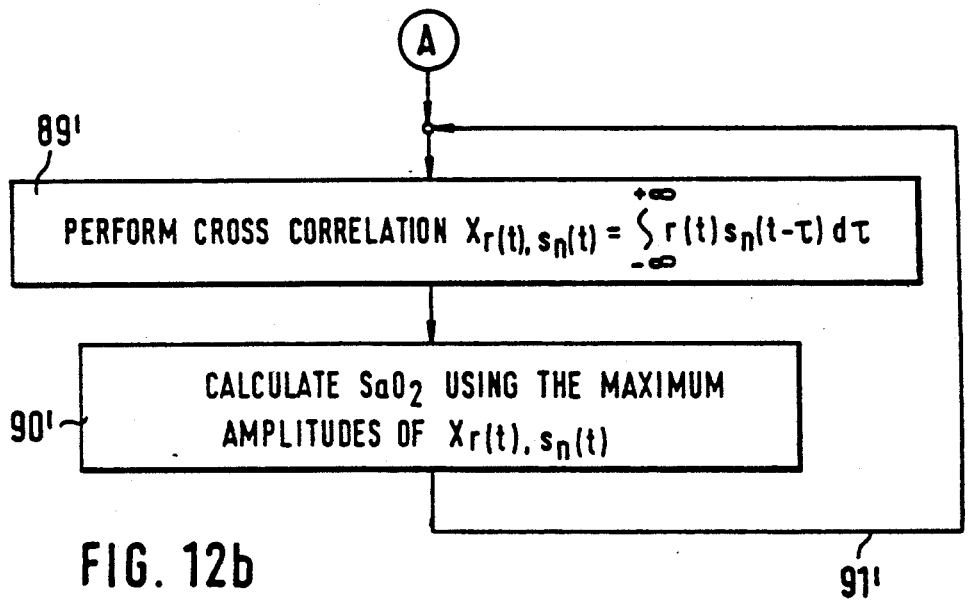
Figure 8:
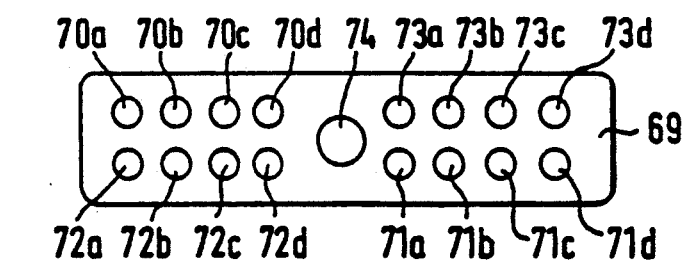
Figure 13A:
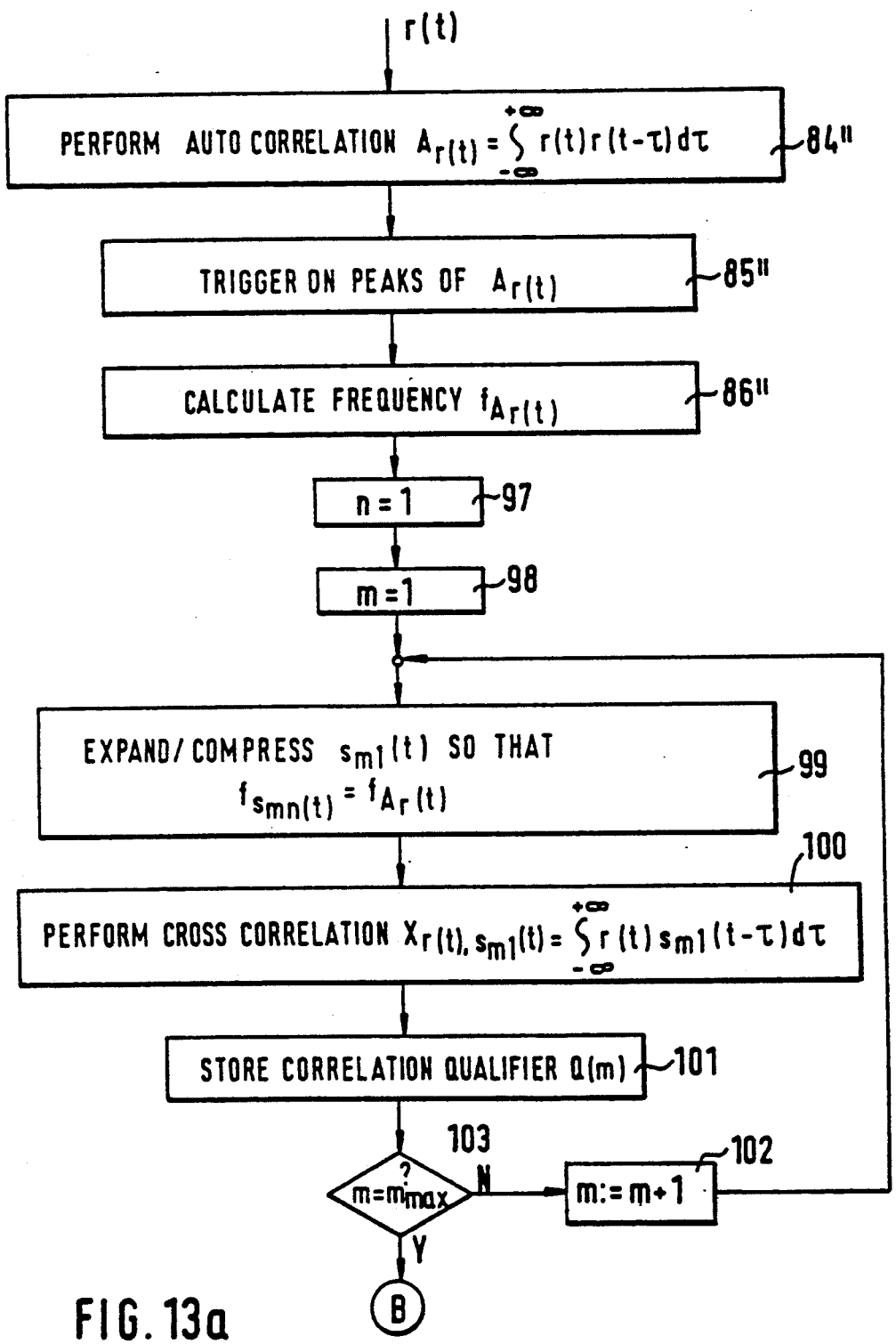
Figure 13B:
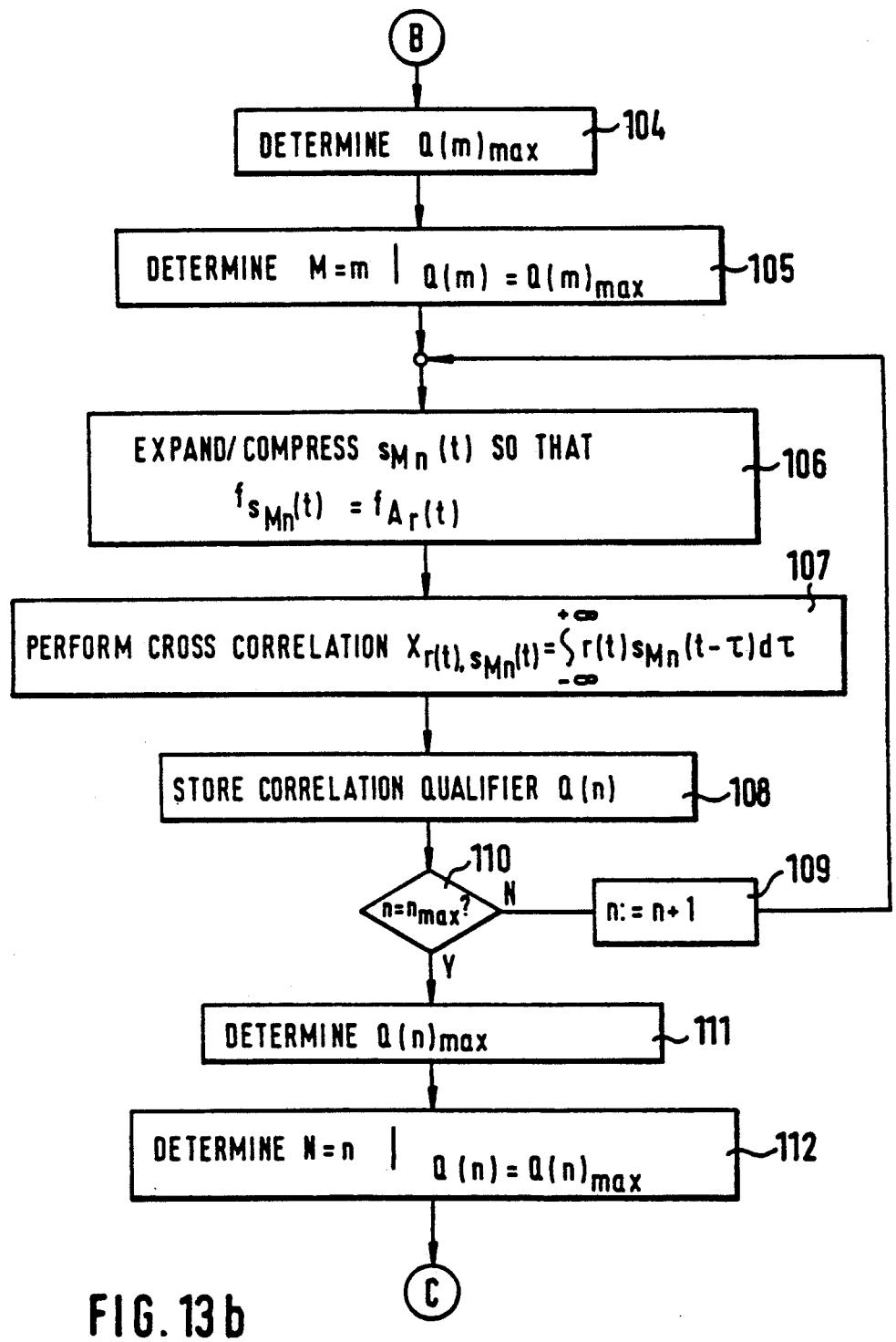
Figure 13C:
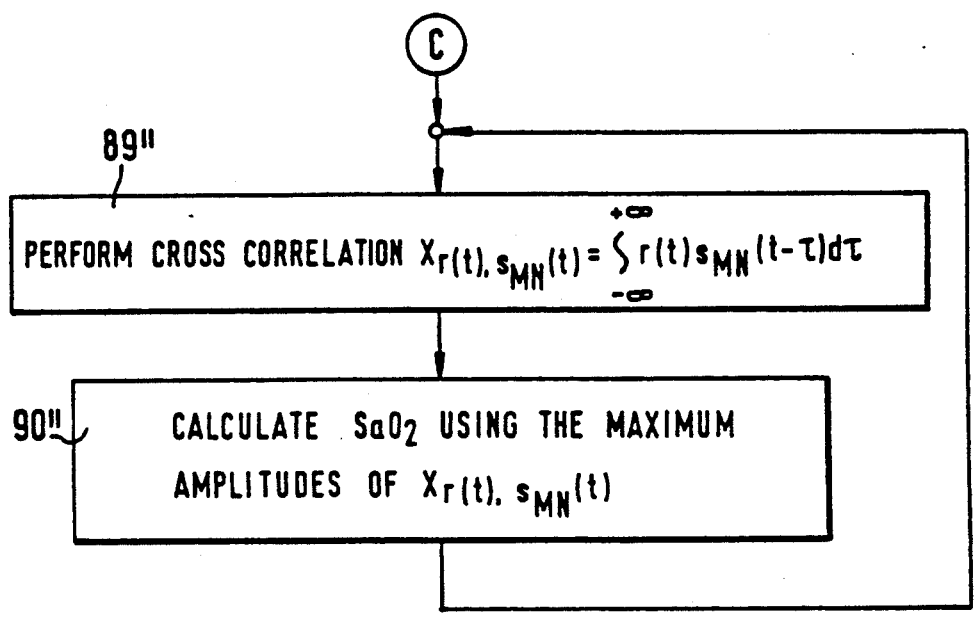

FIG. 5 depicts a cross-section through a reflection sensor for fetal application, FIG. 6 is a block diagram of an oximeter, FIGS. 7a and 7b illustrate an embodiment of a reflection sensor which is designed for adaptance to different applications or tissue characteristics, FIG. 8 depicts the basic arrangement of a self-adapting reflection sensor, FIG. 9 shows a cross-section through a fetal sensor, FIG. 10 is the view of this sensor in the direction of arrow X of FIG. 9, FIG. 11 depicts a basic flow chart for signal improvement using auto- and cross-correlation, FIGS. 12a and 12b depict the basic flow chart of a more sophisticated method of signal improvement and FIGS. 13a to 13c depict the flowchart for signal improvement based on an adaptive process for selection of a pattern signal.

Figure 1:
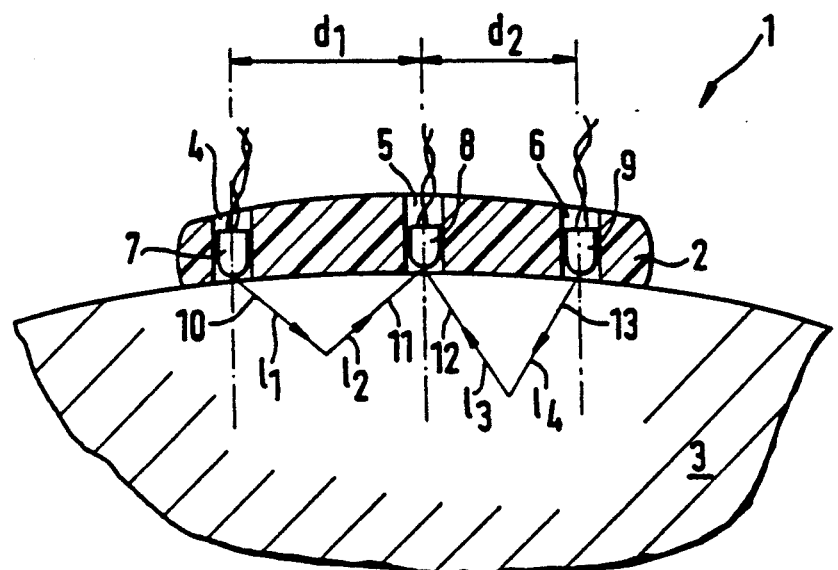
FIG. 1 depicts a cross-section through a simple reflection sensor in order to illustrate the basic concept.

FIG. 1 depicts a cross-section through an oximetry sensor of the reflectance type generally outlined as 1. This sensor comprises a carrier body 2 which is applied to a part of the human body generally designated as 3. Human body part 3 may be the chest, the stomach, a leg etc. of a patient. For centralized patients (i.e. patients in shock), the extremities such as arms or legs cannot be used due to a lack of pulsating blood. This is a particular application where reflection oximetry is required; as transillumination through the chest or the stomach is not possible, only a reflection sensor can be applied.

Although the carrier body 2 is depicted as a one-component part here, it is understood that the carrier means may also consist of several connected or non-connected components. Carrier body 2 may be fixed to the human body in any convenient manner, e.g. using a surgical glue or a self-adhesive tape (not shown here).

Carrier body 2 has three bores 4, 5 and 6. Bores 4 and 6 hold light-emitting diodes (LEDs) 7 and 9, whereas bore 5 houses a photoelectric receiver 8, e.g. a phototransistor or a photodiode. The electrical connection of the wires leading to these LEDs and the photoelectric receiver are not shown in detail here. These connections can be made in usual manner, e.g. they may lead to a connection cable for connection with an appropriate oximeter.

LEDs 7 and 9 emit light of different wavelengths into the human flesh. For example, LED 7 may emit light of a wavelength of 650 nms (red), whereas LED 9 may emit light of a wavelength of 940 nms (infrared). Light emitted by these LEDs is transmitted into the human tissue and reflected as indicated by light paths 10, 11 (red) and 12, 13 (infrared). The reflected light is received by photoelectric receiver 8 which is sensitive to both wavelengths.

As illustrated in FIG. 1, the depth of penetration into human tissue is different between the two wavelengths, i.e. depends on the wavelength. According to the invention, transmitter LEDs 7 and 9 are *not* arranged symmetrically with respect to photoelectric receiver 8. Instead, the distances $d_1$ (distance between LED 7 and receiver 8) and $d_2$ (distance between LED 9 and receiver 8) are not equal.

Distances $d_1$ and $d_2$ are selected such that the length of the red light path ($l_1+l_2$, i.e. the length of light ways 10 and 11) is equal to the infrared light path ($l_3+l_4$, i.e. the length of light ways 12 and 13). As infrared light incorporates a smaller extinction coefficient, i.e. less absorbance and therefore a deeper penetration into human tissue, the infrared LED 9 is placed closer to photoelectric receiver 8 than red LED 7.

By means of the selection $l_1+l_2=l_3+l_4$, the ways of the light at different wavelengths through human tissues are made equal. By this measure, it is ensured that the assumptions of the theory are met and leads to reliable oxygen saturation readings. The oximeter (not shown here) to which sensor 1 is connected measures the intensity, i.e. converts the received signal into an analog voltage and/or a digital value and uses the intensities, particularly their AC and DC components, to calculate oxygen saturation as described above.

If photoelectric receiver 8 is sensitive to both wavelengths, the sensor must be operated in pulsed mode so that at any point in time only one of the light waves is received. It is also possible to use a combined receiver selective to either of the used wavelengths instead; in this case, the transmitter LEDs may be operated continuously.

Distances $d_1$ and $d_2$ are selected such that the condition $l_1+l_2=l_3+l_4$ is met at the place of application for which the sensor is designed. Instead, it is also possible to use average tissue characteristics—i.e. extinction coefficients—to determine $d_1$ and $d_2$; this is particularly useful for a multi-purpose sensor which may be applied to various parts of the human body, e.g. chest, stomach, leg, arm etc.

In the shown example—where the surface of the sensor is relatively flat—identical length of the light paths results in different distances $d_1$ and $d_2$ between the various transmitter LEDs 7, 9 and the photoelectric receiver 8. It has to be emphasized that such is not mandatory; in case of a sensor which is very complex in geometry, it might also happen that the distances between the transmitter LEDs and the photoelectric receiver are equal. Such a sensor is also covered by the scope of the present invention as long as the light paths at the various wavelengths are substantially equal. Furthermore, there may be additional transmitter LEDs which are used to measure further body parameters; it is understood that, for these additional LEDs, the condition of equal length of light paths must not necessarily be met.

Figure 2:
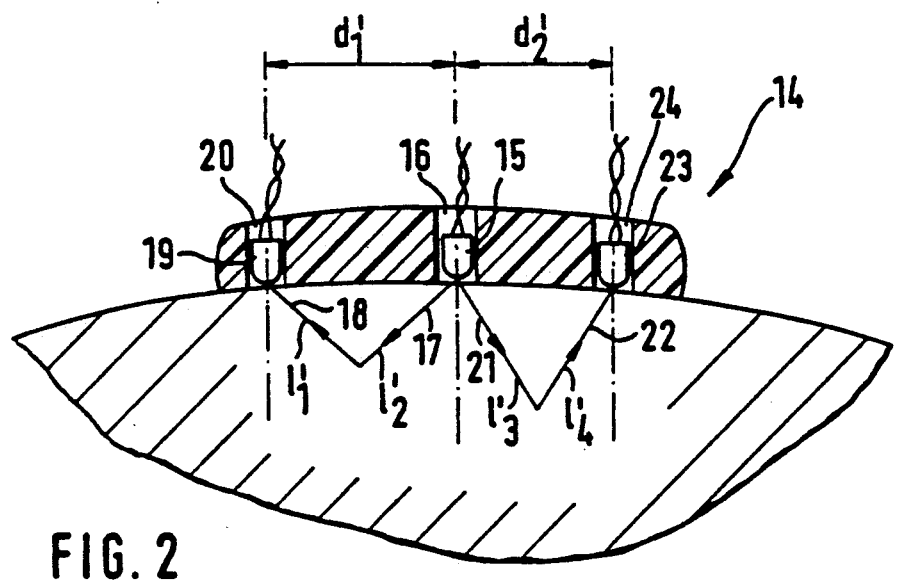
FIG. 2 depicts a second embodiment of such reflection sensor.

FIG. 2 depicts the reversal of the principle shown in FIG. 1. Reflection sensor 14 comprises a transmitter LED 15 housed in bore 16 which is able to emit light of two different wavelengths. The red light (light path 17, 18) is fed to photoelectric receiver 19 housed in bore 20, whereas the infrared light is fed (light path 21, 22) to photoelectric receiver 23 housed in bore 24. Like in FIG. 1, the design of FIG. 2 meets the condition $l_{1'}+l_{2'}=l_{3'}+l_{4'}$. Sensor 14 may be operated continuously or in pulsed manner.

In the sensor shown in FIG. 1, transmitter LEDs 7 and 9 are arranged on opposite sides with respect to photoelectric receiver 8. Likewise, in FIG. 2 photoelectric receivers 19 and 23 are arranged on opposite sides of transmitter LED 15. It is understood that this is not a mandatory feature.

Figure 3:
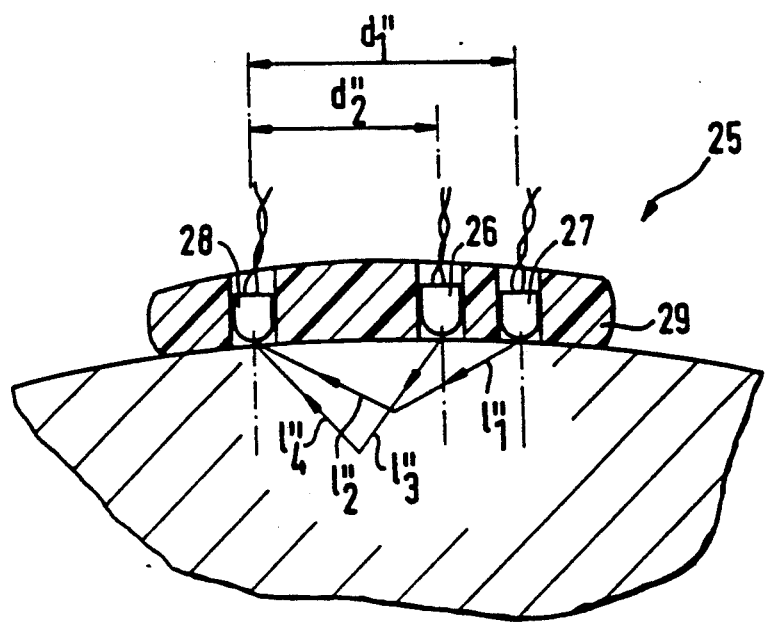
FIG. 3 depicts a third embodiment.

FIG. 3 shows a reflection sensor 25 where transmitter LEDs 26 (infrared) and 27 (red) are arranged on the same side with respect to photoelectric receiver 28. According to the invention, distances $d_1''$ and $d_2''$ are selected such that $l_1''+l_2''=l_3''+l_4''$. The arrangement shown in FIG. 3 allows a more compact and smaller design; particularly, carrier body 29 may have smaller dimensions (not shown here).

Figure 4:
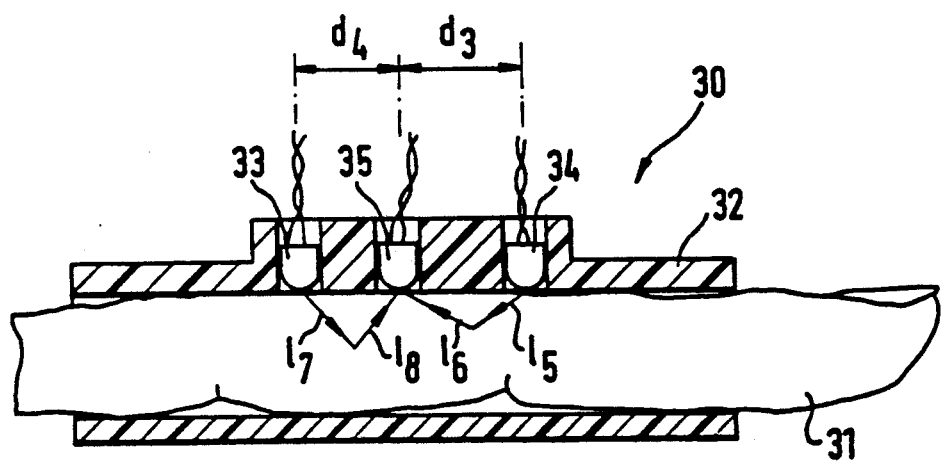
FIG. 4 shows a finger sensor of the reflection type.

Another example of a reflection sensor according to the invention is shown in FIG. 4. The sensor generally outlined as 30 is a finger sensor, i.e. a sensor specifically adapted for application to human finger 31. This sensor comprises a carrier body 32 closed in itself in cross-section and fed over a human finger (in case of neonates, it may also be applied around the neonate's arm). The transmitter LEDs are outlined as 33 (infrared) and 34 (red); reference number 35 depicts the photoelectric receiver. Distances $d_3$ and $d_4$ are selected such that the condition $l_5+l_6=l_7+l_8$ is fulfilled.

The geometry of sensor 30 which is specifically adapted for a certain application—i.e., it cannot be applied to another part of the human body or another human limb than a finger—allows very exact adjustment of distances $d_3$ and $d_4$. As the extinction coefficients of human tissue at a finger are quite precisely known, the condition $l_5+l_6=l_7+l_8$ can be perfectly met. On the other hand, if sensor 30 is also destined for application to the arm of a neonate, average values must be taken. A solution for this problem—i.e. to take the application at an adult finger or a neonatal arm into account—will be discussed later. This also applies if different tissue structures between fingers of different patients shall be considered.

Another sensor adapted to a specific application is fetal sensor 36 shown in FIG. 5. It consists of a carrier body 37 in the form of a suction cup. Suction tube 38 is connected to a suction tube (not shown here). The sensor is applied to the fetal scalp through the vagina; i.e. tissue 39 represents the outer layer of the fetal scalp. By applying underpressure to suction tube 38, the sensor is attached to the scalp (which may also be performed using surgical glue). Transmitter LEDs 40 (infrared) and 41 (red) are placed such with respect to photoelectric receiver 42 that, for the light paths, the condition $l_{5'}+l_{6'}=l_{7'}+l_{8'}$ is met.

FIG. 6 depicts the basic structure of an oximeter, i.e. an apparatus for operating one of the above described sensors. The sensor connected with the oximeter is generally outlined as 43. The signal generated by the photoelectric receiver is fed by a line 44 to a current-/voltage conversion unit 45 and then to an analog-to-digital converter 46 which generates a digital representation of the measured intensity. This digital value is then fed to a microprocessor 47 operating under control of a program memory 48. This program memory contains all necessary code for the processor to calculate oxygen saturation. It also contains program code destined to perform a plausibility check on the received and converted signals. Particularly, said program code may compare the received signals with predefined limits or predefined signals and cause the processor to generate an alarm or a warning message to the user if such limits are exceeded or the predefined signals not met. Such is an indication that either the transducer is applied to the wrong place or that it is not attached securely.

The program code contained in memory 48 may further contain instructions to the processor 47 to compare the received and converted signals with sets of predefined signals each being representative of a certain place of application at the human body or of certain tissue characteristics. Such comparison may e.g. be performed by cross-correlation. It is also possible to perform such comparison on the basis of attenuation values or amplitudes. The program code then instructs the processor to select those of the sets of predefined signals comprising most common characteristics with the received signal.

There may be several reasons for such a check. In case of a sensor which is designed specifically for application to a certain human limb, such check can reveal whether the sensor is applied correctly and in good contact with the human skin. Further, the oximeter can perform self-adaptation to a certain tissue structure (there may be variations in the flesh of e.g. a finger, even from patient to patient). Last not least, in case of a general purpose sensor the place of application may be detected.

The program code therefore instructs processor 47 to correct the received signal in dependency of the selected set which yields considerably better oxygen saturation readings.

Reference is now made to FIG. 7a. Reflection sensor 49 shown in this figure comprises a carrier body 50 with bores 51, 52, 53 and 54. These bores house transmitter LEDs 55, 56 and 58 as well as a photoelectric receiver 57.

Transmitter LEDs 55 and 56 emit light of the same wavelength, whereas transmitter LED 58 transmits light of another wavelength. For example, transmitter LEDs 55 and 56 may emit electromagnetic waves in the red spectrum and transmit LED 58 in the infrared spectrum. Photoelectric receiver 57 is sensitive to both wavelengths.

Such a sensor may be adapted to different places of application or different tissue characteristics. In the example of FIG. 7a, the distance between transmitter LED 55 and photoelectric receiver 57 is selected such that the total length of light path 60, 61 is equal to the total length of light path 62, 63 in a certain tissue—e.g. the chest—59. The other red transmitter LED 56 is positioned such that the total length of light path 64, 65 is equal to the total length of light path 66, 67 in another kind of tissue—e.g. the scalp—68. This is illustrated in FIG. 7b.

It can be readily seen that the depth of penetration, and therefore also the length of the light paths, varies for each wavelength with the kind of tissue. Nevertheless, with the design depicted in FIGS. 7a and 7b, it is possible to adapt the sensor to the specific application. Adaptation may be performed for two different purposes: first, a general-purpose sensor may be adapted to a certain place of application, and/or second, a distinction can be made between different tissue structures, even if the place of application is the same (e.g. the chest), but the characteristics of the tissue varies from patient to patient.

The selection among transmitter LEDs 55 and 56 may be performed by the oximeter in different ways. First, there may be provided selection input means for selecting the place of application at the human body, i.e. the user may enter the place of application (and/or other characteristics of the measurement, e.g. the age of the patient). The oximeter comprises transmitter selection means responsive to the selection input means and selects the appropriate transmitter. Furthermore, the oximeter may comprise plausibility checking means for comparison of the received signals with predefined limits or predefined signals representative of the selected place of application. If a considerable deviation is detected, an alarm or a warning message may be generated as, in such case, it is likely that the user has entered the wrong place of application.

Alternatively, the oximeter may also provide automatic selection of those transmitters which are best suited for a certain application or tissue. Such oximeter selects sequentially all of the available transmitters and/or receivers, i.e. tests all possible light paths. The signals received in any case are compared with sets of predefined signals which are representative of certain places of application at the human body or of certain tissue characteristics. Such comparison may be e.g. performed by cross-correlation. For each transmitter/receiver combination, i.e. for each light path, the degree of correspondence (e.g. the maximum of the cross-correlation function) is stored. When all tests have been performed, the transmitter/receiver combination with the highest degree of correspondence is selected, and further measurements are performed with the associated transmitter/receiver.

It is understood that the above principles for sensor construction and oximeter operation may also be "reversed" in the sense that not multiple transmitter LEDs of the same wavelength are provided (like LEDs 55, 56 in FIGS. 7a and 7b), but a multiplicity of receivers instead. A further possibility is to provide a multiplicity of transmitter LEDs of one wavelength and a further multiplicity of transmitter LEDs of a second wavelength.

Such a sensor is depicted in FIG. 8. Carrier body 69 comprises red LEDs 70a to 70d and 71a to 71d as well as infrared LEDs 72a to 72d and 73a to 73d. The photoelectric receiver is outlined as 74. Such a sensor may be used, in conjunction with an appropriate oximeter, for very precise manual or automatic adaptation to different kinds of measurement by selecting an appropriate red LED/infrared LED combination.

A fetal sensor for appliance to the fetal skin and embodying this principle is depicted in FIGS. 9 and 10. Sensor case 75 is connected with an oximeter (not shown here) via cable 76. A suction tube 77 is connected with a nozzle 78 which provides connection with a suction ring 79. A suction chamber 80 is in contact with the fetal skin and holds the sensor to it if underpressure is applied to the chamber.

Centrally arranged in the sensor are two infrared LEDs 81a and 81b, two red LEDs 82a and 82b as well as a photoelectric receiver 83. Due to the different distances between the LEDs of each wavelength and the photoelectric receiver, adaptation to different tissue characteristics may be performed (as outlined above), either manually or on an automatic basis. The sensor shown in FIGS. 9 and 10 may also comprise electrocardiogram contacts (although not shown here).

Reference is now made to FIG. 11. In this figure, r(t) represents a received signal, i.e. a signal received by a photoelectric receiver. According to box 84, an autocorrelation is performed on this signal. A known feature of autocorrelation is that specific properties of a periodic signal are amplified; in the present case, the event of interest is the occurrence of the arterial blood pulse.

It is therefore possible to trigger on the peaks, i.e. high amplitudes, of the autocorrelation function $A_{r(t)}$. This is indicated by box 85. As the amplitudes of the received signal representing the arterial blood pulse are higher in the autocorrelation function—with respect to any noise or artefacts contained therein—compared to the original signal r(t), it is easier to find the peaks associated with the arterial blood pulse.

The detected peaks are used to calculate the frequency of the autocorrelation function—and, therefore, also of the original signal r(t)—in that the time delay between subsequent peaks is measured, and the frequency is calculated as the reverse of this time delay. This is illustrated in the flow chart of FIG. 11 by box 86. As the arterial blood pulse is a result of the heart beat, the calculated frequency represents the heart rate (box 87). The method described in FIG. 11 therefore provides a solution to calculate the heart rate—here as a by-product of oxygen saturation calculation—without electrocardiogram electrodes and without any need for additional electronics to process the ECG.

The method described in FIG. 11 further provides a predefined or pattern function s(t). This pattern function represents an ideal signal for the selected application. According to box 88, the periodic function s(t) is now expanded or compressed such that its frequency is substantially equal to the frequency of the autocorrelation function $A_{r(t)}$ or—which is the same—of the received signal r(t). In a digital environment, expansion may e.g. be performed by interpolation between subsequent samples of s(t), whereas compression may be performed in that certain samples of s(t) are cancelled on a periodic basis.

The oximeter has now calculated an optimum function for the received signal, both representing the same frequency. During their measurement cycle, the oximeter performs then a cross-correlation on the received signal and the optimum function as depicted in box 89. By means of such cross-correlation, expected—i.e. wanted—components are passed, and unexpected components in the signal (like artefacts) are removed. Therefore, the maximum (and/or minimum) amplitudes of the cross-correlation function are used to calculate oxygen saturation reliably, even if the original signal r(t) contained superimposed artefacts or was distorted by noise. Oxygen saturation calculation is indicated by box 90.

As indicated by line 91, the cross-correlation function is calculated on an ongoing basis (for a new signal r(t)) in order to determine the oxygen saturation as long as measuring continues.

It is understood that the equations given in boxes 84 and 89 for the autocorrelation and the cross-correlation function are "ideal" equations. In practical applications, it is not possible to integrate to infinity, and further, integration may be substituted by digital summation. Such techniques are well-known in the art.

An even more sophisticated method of signal improvement is depicted in FIGS. 12a and 12b. Boxes which are functionally equivalent to the method depicted in FIG. 11 are labelled with the same reference numbers, but with an additional apostrophe.

Whereas the method shown in FIG. 11 provides only one optimum function s(t) (or a set of optimum functions, wherein one of the functions contained therein is selected upon application entry by the user), the method depicted in FIGS. 12a and 12b provides automatic adaptation to a certain application or tissue. For this purpose, the method provides a multiplicity of n optimum functions $S_{n(t)}$ (also called "sets" of pattern signals).

Each of the pattern functions $S_{n(t)}$ is subsequently expanded or compressed so that it incorporates the same frequency as the autocorrelation function, and then it is cross-correlated with r(t). Whenever the correlation is satisfying, i.e. the maximum amplitude or the average value of the cross-correlation function exceeds a certain limit, the oximeter assumes that it has detected the place of application or the tissue characteristics and performs further measurements on the basis of a cross-correlation with this reference function.

This basic operating scheme will now be explained according to the flow charts of FIGS. 12a and 12b. According to FIG. 12a, a counter n representing an index is first set to 1 (box 92). Then, the pattern signal $s_{n(t)}$ (with n as defined above) is expanded or compressed so that it incorporates the same frequency as the autocorrelation function (box 93). Thereafter, a cross-correlation is performed on r(t) and $s_{n(t)}$ (box 94), and the degree of correlation is assessed (reference number 95). As outlined above, selection criteria may e.g. be the height of the maximum peak in the cross-correlation function, its average value, its integral over one period, the correlation coefficient etc.

If the correlation is not satisfying, n is increased by 1 (box 96), and the process starts again with the next pattern signal. (The flow chart of FIG. 12a does not show the case that no satisfying correlation is found among all of the available pattern signals. It is understood that, in such case, either an error message has to be generated, or the pattern signal with the highest degree of correlation has to be selected).

Whenever a satisfying correlation is detected, operation proceeds to label "A", and further measurements are performed by a cross-correlation between the received signal r(t) and the selected pattern function $s_{n(t)}$ (FIG. 12b).

Instead of the assessment of the pattern functions as depicted in FIGS. 12a and 12b, it is also possible to calculate the correlation between r(t) and *all* pattern functions and select the pattern function with the highest degree of correlation. Such a more sophisticated method is illustrated in FIGS. 13a to 13c. To reduce the time necessary to select a certain pattern function, the method according to FIGS. 13a to 13c uses an approximation algorithm. The pattern functions are preselected in groups, each group representing a certain characteristics. r(t) is first cross correlated with one pattern function of each group ("group pattern function"—this function is typical for the represented group). Then, the group pattern function—and, therefore, the group—with the highest degree of correlation with r(t) is selected. In a second step, r(t) is cross correlated with each member of the selected group ("fine tuning"), and the member with the highest degree of correlation is then selected as reference pattern function.

In FIG. 13a, reference numbers 84", 85" and 86" denote the same functions as in FIGS. 11 and 12a, i.e. autocorrelation, peak trigger and frequency calculation. The method according to FIG. 13 uses two counters or indices, n and m, which are set to 1 in steps 97 and 98. "m" is a counter associated with groups of pattern functions, whereas "n" is a counter associated with the single pattern functions in a group.

The first step is to determine the group incorporating most common attributes with r(t). For this purpose, the first pattern function $s_{m1}(t)$ in a group—which is selected as a typical example of this group and incorporates the major characteristics of this group—is expanded/compressed so that it has the same frequency, i.e. the same period, as $A_{r(t)}$ (step 99). Then, r(t) is cross correlated with $s_{m1}(t)$ (step 100). According to step 101, the degree of common characteristics with r(t) (e.g. the correlation coefficient)—here called correlation qualifier Q(m)—is stored.

The cross correlation according to step 100 is performed for all available groups, i.e. counter m is increased (reference number 102) until m reaches its maximum (reference number 103).

When all cross correlations are processed, the highest correlation qualifier $Q(m)_{max}$ is determined (step 104, FIG. 13b) from all correlation qualifiers stored during the preceding process. Its associated counter or index m is now set to M (step 105). M represents the selected group, i.e. the group with most common characteristics with r(t).

The next block describes the selection of a certain member (pattern function) from group M. Only pattern functions $s_{Mn}(t)$—i.e. pattern functions contained in the selected group—are regarded during this process. Like in the preceding block, $s_{Mn}(t)$ is expanded/compressed in order to represent the same frequency as $A_{r(t)}$ (step 106), and a cross correlation is performed on r(t) and $s_{Mn}(t)$ (step 107). The correlation qualifier Q(n) is stored (step 108), and the process is repeated for all members of the selected group, i.e. n is increased (step 109) until n reaches its maximum (step 110). Qualifier $Q(n)_{max}$ (highest degree of correlation) is selected (step 111), and its associated counter or index n represents the index N of the pattern function selected from the selected group (step 112).

Selection of a pattern function is now complete. From all available pattern functions $s_{mn}(t)$, $s_{MN}(t)$ is the pattern function used for cross correlation with r(t) during the following measurement. This is illustrated in blocks 89" and 90" (FIG. 13c) which are identical to the corresponding blocks in FIGS. 11 and 12b.

I claim:

1. A sensor for noninvasive measurement of oxygen saturation by irradiating human tissue with electromagnetic waves and measuring the intensity of the reflected waves comprising:
   (1.1) carrier means;
   (1.2) at least two transmitter means for emitting electromagnetic waves of different wavelengths into the human tissue and mounted on said carrier means; and
   (1.3) at least one receiver means disposed on said carrier means for receiving electromagnetic waves of said different wavelengths reflected from the human tissue, said at least two transmitters mounted on said carrier means at distances from said receiver selected such that the lengths of the electromagnetic wave paths through the human tissue at both different wavelengths are substantially equal.

2. A sensor according to claim 1 wherein said carrier means is geometrically shaped for application to a specific part of the human body, and that the distances between the transmitter and the receiver are determined based on average values of tissue characteristics of said specific human body part, selected such that the electromagnetic wave paths at at least two different wavelengths, are substantially equal.

3. A sensor according to claim 2 for measuring oxygen saturation of a fetus prior to and during birth, wherein said carrier means is a cap comprising at least two transmitting light emitting diodes, emitting electromagnetic waves of different wavelengths, and at least one receiver responsive to said different wavelengths.

4. A sensor according to claim 3, wherein said cap is a suction cup comprising a suction tube connected with a suction source.

5. A sensor according to claim 2, wherein said carrier means if substantially closed on itself in cross-section for application to a finger of an adult person.

6. Apparatus for noninvasive measurement of oxygen saturation for connection to a sensor according to claim 2 further comprising conversion means for converting the intensity of the received electromagnetic waves into electrical signals; processing means for calculating oxygen saturation from said electrical signals; and plausibility checking means for comparing the received signals with predefined limits or predefined signals and for generating an alarm or a warning message upon a significant deviation.

7. Apparatus for noninvasive measurement of oxygen saturation for connection to a sensor, particularly according to claim 2, further comprising conversion means for converting the intensity of the received electromagnetic waves into electrical signals; comparison means for comparing said electrical signals with sets of predefined signals representative of certain places of application at the human body or representative of certain tissue characteristics and for selecting the set having the most common characteristics with said electrical signals; correction means for correcting said electrical signals in dependency of the selected set; and processing means for the calculation of oxygen saturation from said corrected electrical signals.

8. Apparatus according to claim 7, wherein said sets of predefined signals contain attenuation values representative of certain places of application of electromagnetic waves to the human body or of certain human tissue.

9. Apparatus according to claim 7, wherein said sets of predefined signals contain values of the amplitude of the alternating component representative of certain places of application of electromagnetic waves to the human body or of certain human tissue.

10. Apparatus according to claim 7, wherein said sets of predefined signals contain signal shapes representative of certain places of application of electromagnetic waves to the human body or of certain human tissue.

11. A sensor according to claim 1, further comprising at least one first transmitter emitting electromagnetic waves of a first wavelength and at least two second transmitters emitting electromagnetic waves of a second wavelength, wherein said first and second transmitters are mounted on said carrier means at different distances to said at least one receiver such that the length of the electromagnetic wave path through the human tissue between said first transmitter and said receiver is for tissue with a certain predefined characteristics substantially equal to the length of the light path through the human tissue between the first of said second transmitters and said receiver whereas the length of the light path through the human tissue between said first transmitter and said receiver is for tissue with another certain predefined characteristic is substantially equal to the length of the light path through the human tissue between the second of said second transmitters and said receiver.

12. A sensor according to claim 11, wherein it comprises 2n first transmitters and 2n second transmitters arranged symmetrically with respect to the receiver, n being an integer number with $n \geq 1$.

13. Sensor according to claim 11, wherein said carrier means are geometrically shaped for application to a specific part of the human body.

14. A sensor according to claim 13 for measuring oxygen saturation of a fetus prior to and during birth, wherein said carrier means is a cap comprising at least two first light emitting diode transmitters emitting electromagnetic waves of a certain first wavelength, and at least two second light emitting diode transmitters emitting electromagnetic waves of a certain second wavelength, and at least one receiver responsive to said different wavelengths.

15. Sensor according to claim 14, wherein said cap is a suction cup comprising a suction tube connected with a suction source.

16. Apparatus for noninvasive measurement of oxygen saturation for connection to a sensor, according to claim 11, further comprising: conversion means for converting the intensity of the received electromagnetic waves into electrical signals; processing means for the calculation of oxygen saturation from said electrical signals, selection input means for selecting the place of application on the human body; and transmitter/receiver selection means responsive to said selection input means and operable to select certain transmitters depending on the place of application.

17. Apparatus according to claim 16, further comprising plausibility checking means for comparing the received signals with predefined limits or predefined signals representative of the selected place of application and for generating an alarm or a warning message upon a significant deviation.

18. Apparatus for noninvasive measurement of oxygen saturation for connection to a sensor, particularly according to claim 11 further comprising: conversion means for converting the intensity of received electromagnetic waves into electrical signals; processing means for the calculation of oxygen saturation from said electrical signals; and application detection means set up to select sequentially certain transmitters to compare each of the specific electrical signals associated with a certain transmitter with sets of predefined signals representative of certain places of application on the human body or representative of certain tissue characteristics and to select those of said specific electrical signals having the most common characteristics with a certain of said sets, and selection means for selecting the transmitter associated with said specific electrical signals having the most common characteristics with a certain of said sets, for further measurement.

19. A sensor for noninvasive measurement of oxygen saturation by irradiating human tissue with electromagnetic waves and measuring the intensity of the reflected waves comprising:
(2.1) carrier means;
(2.2) at least one transmitter means emitting electromagnetic waves of different wavelengths into the human tissue and mounted on said carrier means,
(2.3) at least two receiver means disposed on said carrier means, each of the receivers being sensitive to at least one of said different wavelengths reflected from the human tissue, said at least two receivers mounted on said carrier means at distances from said transmitter selected such that the lengths of the electromagnetic wave paths through the human tissue, at both different wavelengths, are substantially equal.

20. A sensor according to claim 19 wherein said carrier means is geometrically shaped for application to a specific part of the human body, and that the distance between the transmitter and receiver are determined based on average values of tissue characteristics of said specific human body part selected such that the electromagnetic wave path at at least two different wavelengths, are substantially equal.

21. Sensor according to claim 20 for measuring oxygen saturation of a fetus prior to and during birth, wherein said carrier means is a cap comprising at least two transmitting light emitting diodes, emitting electromagnetic waves of different wavelengths, and at least one receiver responsive to said different wavelengths.

22. Sensor according to claim 21 wherein said cap is a suction cup comprising a suction tube connected with a suction source.

23. A sensor according to claim 20 wherein said carrier means is substantially closed on itself in cross-section for application to a finger of an adult person.

24. Apparatus for noninvasive measurement of oxygen saturation for connection to a sensor according to claim 20 further comprising conversion means for converting the intensity of the received electromagnetic waves into electrical signals; processing means for the calculating of oxygen saturating from said electrical signals; and plausibility checking means for comparing the received signals with predefined limits or predefined signals and for generating an alarm or a warning message upon a significant deviation.

25. Apparatus for noninvasive measurement of oxygen saturation for connection to a sensor, particularly according to claim 20 further comprising: conversion means for converting the intensity of the received electromagnetic waves into electrical signals; comparison means for comparing said electrical signals with sets of predefined signals representative of certain places of the application at the human body or representative of certain tissue characteristics and for selecting the set having the most common characteristics with said electrical signals; correction means for correcting said electrical signals in dependency of the selected set; and processing means for the calculation of oxygen saturation from said corrected electrical signals.

26. Apparatus according to claim 25 wherein said sets of predefined signals contain attenuation values representative of certain places of application of electromagnetic waves to the human body or of certain human tissue.

27. Apparatus according to claim 25 wherein said sets of predefined signals contain values of the amplitude of the alternating component representative of certain places of application of electromagnetic waves to the human body or of certain human tissue.

28. Apparatus according to claim 25 wherein said sets of predefined signals contain signal shapes representative of certain places of application of electromagnetic waves to the human body or of certain human tissue.

29. A sensor according to claim 19 further comprising at least one first receiver disposed to receive electromagnetic waves of a first wavelength and at least two second receivers disposed to receive electromagnetic waves of a second wavelength, wherein said first and second receivers are mounted on said carrier means at different distances from said at least one transmitter such that the length of the light path through the human tissue between said transmitter and said first receiver is for tissue with a certain predefined characteristics substantially equal to the length of the light path through the human tissue between said transmitter and the first of said second receivers, whereas the length of the light path through the human tissue between said transmitter and said first receiver is for tissue with another certain predefined characteristics substantially equal to the length of the light path through the human tissue between said transmitter and the second of said second receivers.

30. Sensor according to claim 29 wherein said carrier means are geometrically shaped for application to a specific part of the human body.

31. Sensor according to claim 30 for measuring oxygen saturation of a fetus prior to and during birth, wherein said carrier means is a cap comprising at least two first light emitting diode transmitters emitting electromagnetic waves of a certain first wavelength, and at least two second light emitting diode transmitters emitting electromagnetic waves of a certain second wavelength, and at least one receiver responsive to said different wavelengths.

32. A sensor according to claim 31 wherein said cap is a suction cup comprising a suction tube connected with a suction source.

33. Apparatus for noninvasive measurement of oxygen saturation for connection to a sensor, particularly according to claim 29 further comprising: conversion means for converting the intensity of the received electromagnetic waves into electrical signals; processing means for the calculation of oxygen saturation from said electrical signals, selection input means for selecting the place of application on the human body, and transmitter/receiver selection means responsive to said selection input means and operable to select certain receiver depending on the place of application.

34. Apparatus according to claim 33 further comprising plausibility checking means for comparing the received signals with predefined limits or predefined signals representative of the selected place of application and for generating an alarm or a warning message upon a significant deviation.

35. Apparatus for noninvasive measurement of oxygen saturation for connection to a sensor, particularly according to claim 29 further comprising: conversion means for converting the intensity of received electromagnetic waves into electrical signals; processing means for the calculation of oxygen saturation from said electrical signals; and application detection means set up to select sequentially certain receivers to compare each of the specific electrical signals associated with a certain receiver with sets of predefined signals representative of certain places of application on the human body or representative of certain tissue characteristics and to select those of said specific electrical signals having the most common characteristics with a certain of said sets, and selection means set up to select the receivers associated with said specific electrical signals having the most common characteristics with a certain of said sets, for further measurement.

36. A sensor for noninvasive measurement of oxygen saturation by irradiating human tissue with electromagnetic waves and measuring the intensity of the reflected waves comprising:

carrier means;
transmitter means for emitting electromagnetic waves of different wavelengths into said human tissue and mounted on said carrier means; and
receiver means disposed on said carrier means for receiving electromagnetic waves of said different wavelengths reflected from said human tissue, said transmitter means and receiver means mounted on said carrier means at distances from each other such that the lengths of the electromagnetic wave paths through the human tissue at both said different wavelengths are substantially equal.

* * * * *